US 8,158,372 B2

(12) United States Patent
Behrens et al.

(10) Patent No.: US 8,158,372 B2
(45) Date of Patent: Apr. 17, 2012

(54) AGONISTS OF A BITTER TASTE RECEPTOR AND USES THEREOF

(75) Inventors: Maik Behrens, Nuthetal (DE); Anne Brockhoff, OT Lemsel (DE); Bernd Bufe, Ferch (DE); Christina Kuhn, Nuthetal (DE); Wolfgang Meyerhof, Norderstedt (DE); Marcel Winnig, Neu Fahrland (DE)

(73) Assignee: Deutsches Institut für Ernährungsforschung Potsdam-Rehbrücke, Nuthetal (DE)

( * ) Notice: Subject to any disclaimer, the term of this patent is extended or adjusted under 35 U.S.C. 154(b) by 649 days.

(21) Appl. No.: 11/578,013

(22) PCT Filed: Apr. 20, 2005

(86) PCT No.: PCT/EP2005/004246
§ 371 (c)(1),
(2), (4) Date: Sep. 3, 2009

(87) PCT Pub. No.: WO2005/102311
PCT Pub. Date: Nov. 3, 2005

(65) Prior Publication Data
US 2010/0056621 A1 Mar. 4, 2010

(30) Foreign Application Priority Data
Apr. 20, 2004 (EP) .................................. 04009346

(51) Int. Cl.
G01N 33/567 (2006.01)
C07K 14/705 (2006.01)
C12N 15/12 (2006.01)

(52) U.S. Cl. .......... 435/7.21; 435/7.1; 435/7.2; 436/501

(58) Field of Classification Search ........................ None
See application file for complete search history.

(56) References Cited

FOREIGN PATENT DOCUMENTS
WO    WO 2004/029087    4/2004

OTHER PUBLICATIONS

Behrens M., et al., "The human taste receptor hTAS2R14 responds to a variety of different bitter compounds", Biochemical and Biophysical Research Communications, (2004) pp. 479-485, vol. 319, No. 2, United States.
Belitz, H.D., et al., "Bitter compounds: occurrence and structure-activity relationships", Food Reviews International 1985 Inst. For Lebensmittelchem, (1985) pp. 271-354, vol. 1, No. 2, Federal Republic of Germany, XP009052930.
Falbe, J., Regitz M, "Römpp Chemie Lexikon", 9th Edition Georg Thieme Verlag (1991) pp. 3437, XP-002342395.

Primary Examiner — John Ulm
(74) Attorney, Agent, or Firm — Saliwanchik, Lloyd & Eisenschenk

(57) ABSTRACT

The present invention relates to agonists of the hTAS2R14 bitter taste receptor and its role in bitter taste transduction. The invention also relates to assays for screening molecules that modulate, e.g. suppress or block hTAS2R14 bitter taste transduction or bitter taste response.

3 Claims, 2 Drawing Sheets

SEQUENCE LISTING

<160> NUMBER OF SEQ ID NOS: 6

<210> SEQ ID NO 1
<211> LENGTH: 317
<212> TYPE: PRT
<213> ORGANISM: Homo sapiens

<400> SEQUENCE: 1

```
Met Gly Gly Val Ile Lys Ser Ile Phe Thr Phe Val Leu Ile Val Glu
1               5                   10                  15

Phe Ile Ile Gly Asn Leu Gly Asn Ser Phe Ile Ala Leu Val Asn Cys
            20                  25                  30

Ile Asp Trp Val Lys Gly Arg Lys Ile Ser Ser Val Asp Arg Ile Leu
        35                  40                  45

Thr Ala Leu Ala Ile Ser Arg Ile Ser Leu Val Trp Leu Ile Phe Gly
    50                  55                  60

Ser Trp Cys Val Ser Val Phe Phe Pro Ala Leu Phe Ala Thr Glu Lys
65                  70                  75                  80

Met Phe Arg Met Leu Thr Asn Ile Trp Thr Val Ile Asn His Phe Ser
                85                  90                  95

Val Trp Leu Ala Thr Gly Leu Gly Thr Phe Tyr Phe Leu Lys Ile Ala
            100                 105                 110
```

Asn Phe Ser Asn Ser Ile Phe Leu Tyr Leu Lys Trp Arg Val Lys Lys
        115                 120                 125

Val Val Leu Val Leu Leu Val Thr Ser Val Phe Leu Phe Leu Asn
130                 135                 140

Ile Ala Leu Ile Asn Ile His Ile Asn Ala Ser Ile Asn Gly Tyr Arg
145                 150                 155                 160

Arg Asn Lys Thr Cys Ser Ser Asp Ser Ser Asn Phe Thr Arg Phe Ser
                165                 170                 175

Ser Leu Ile Val Leu Thr Ser Thr Val Phe Ile Phe Ile Pro Phe Thr
            180                 185                 190

Leu Ser Leu Ala Met Phe Leu Leu Leu Ile Phe Ser Met Trp Lys His
        195                 200                 205

Arg Lys Lys Met Gln His Thr Val Lys Ile Ser Gly Asp Ala Ser Thr
    210                 215                 220

Lys Ala His Arg Gly Val Lys Ser Val Ile Thr Phe Phe Leu Leu Tyr
225                 230                 235                 240

Ala Ile Phe Ser Leu Ser Phe Phe Ile Ser Val Trp Thr Ser Glu Arg
                245                 250                 255

Leu Glu Glu Asn Leu Ile Ile Leu Ser Gln Val Met Gly Met Ala Tyr
            260                 265                 270

Pro Ser Cys His Ser Cys Val Leu Ile Leu Gly Asn Lys Lys Leu Arg
        275                 280                 285

Gln Ala Ser Leu Ser Val Leu Leu Trp Leu Arg Tyr Met Phe Lys Asp
    290                 295                 300

Gly Glu Pro Ser Gly His Lys Glu Phe Arg Glu Ser Ser
305                 310                 315

<210> SEQ ID NO 2
<211> LENGTH: 951
<212> TYPE: DNA
<213> ORGANISM: Homo sapiens

<400> SEQUENCE: 2
atgggtggtg tcataaagag catatttaca ttcgttttaa ttgtggaatt tataattgga      60
aatttaggaa atagtttcat agcactggtg aactgtattg actgggtcaa gggaagaaag     120
atctcttcgg ttgatcggat cctcactgct ttggcaatct ctcgaattag cctggtttgg     180
ttaatattcg gaagctggtg tgtgtctgtg ttttttccag ctttatttgc cactgaaaaa     240
atgttcagaa tgcttactaa tatctggaca gtgatcaatc attttagtgt ctggttagct     300
acaggcctcg gtacttttta ttttctcaag atagccaatt tttctaactc tattttttctc    360 tacctaaagt ggagagttaa aaaggtggtt tggtgctgc ttcttgtgac ttcggtcttc      420
ttgtttttaa atattgcact gataaacatc catataaatg ccagtatcaa tggatacaga     480
agaaacaaga cttgcagttc tgattcaagt aactttacac gattttccag tcttattgta     540
ttaaccagca ctgtgttcat tttcataccc tttactttgt ccctggcaat gtttcttctc     600
ctcatcttct ccatgtggaa acatcgcaag aagatgcagc acactgtcaa atatccgga      660 gacgccagca ccaaagccca cagaggagtt aaaagtgtga tcactttctt cctactctat     720
gccatttcct ctctgtcttt ttcatatca gtttggacct ctgaaaggtt ggaggaaat     780 ctaattattc tttcccaggt gatgggaatg gcttatcctt catgtcactc atgtgttctg     840
attcttggaa acaagaagct gagacaggcc tctctgtcag tgctactgtg gctgaggtac     900
atgttcaaag atggggagcc ctcaggtcac aaagaattta gagaatcatc t              951

```
<210> SEQ ID NO 3
<211> LENGTH: 45
<212> TYPE: DNA
<213> ORGANISM: Artificial
<220> FEATURE:
<223> OTHER INFORMATION: Forward primer for amplification of hTAS2R14,
      which introduces a restriction site

<400> SEQUENCE: 3
ggccaattgg aattcatggg tggtgtcata aagagcatat ttaca            45

<210> SEQ ID NO 4
<211> LENGTH: 56
<212> TYPE: DNA
<213> ORGANISM: Artificial
<220> FEATURE:
<223> OTHER INFORMATION: Backward primer for amplification of hTAS2R14,
      which introduces a restriction site

<400> SEQUENCE: 4
tcctcaattg tcatcagcgg ccgccagatg attctctaaa ttctttgtga cctgag   56

<210> SEQ ID NO 5
<211> LENGTH: 20
<212> TYPE: DNA
<213> ORGANISM: Homo sapiens

<400> SEQUENCE: 5
accacagtcc atgccatcac                                        20

<210> SEQ ID NO 6
<211> LENGTH: 21
<212> TYPE: DNA
<213> ORGANISM: Homo sapiens

<400> SEQUENCE: 6
tcccaccacc ctgttgctgt a                                      21
```

AGONISTS OF A BITTER TASTE RECEPTOR AND USES THEREOF

CROSS-REFERENCE TO RELATED APPLICATION

This application is the U.S. national stage application of International Patent Application No. PCT/EP2005/004246, filed Apr. 20, 2005, the disclosure of which is hereby incorporated by reference in its entirety, including all figures, tables and amino acid or nucleic acid sequences.

BACKGROUND

Investigators have recently turned their attention to understanding the biological mechanisms of taste, and in particular bitter taste. For a review of the literature see, for example, Caicedo A. and Roper S. D. (2001) Science 291: 1557-1560; Dulac C. (2000) Cell 100: 607-610; Kinnamon S. C. (2000) Neuron 25: 507-510; Lindemann B. (2001) Nature 413: 219-225.; and Margolskee R F. (2001) J. Biol. Chem. 277: 1-4.

Bitter taste is aversive, and as such provides humans with a mechanism of protection against poisonous substances, which are generally bitter-tasting compounds. More subtly, bitter-tastants also affect the palatability of food, beverages, thereby influencing human nutritional habits as is more fully discussed by Drewnowski in "The Science and Complexity of Bitter Taste", (2001) Nutr. Rev. 59: 163-169. They also affect the palatability of other ingestibles such as orally administered pharmaceuticals and nutraceuticals. Understanding the mechanism of bitter taste transduction has implications for the food and pharmaceutical industries. If the bitter taste transduction pathway can be manipulated, it may be possible to suppress or eliminate bitter taste to render foods more palatable and increase patient compliance with oral pharmaceutics.

Taste transduction involves the interaction of molecules, i.e., tastants with taste receptor-expressing cells which reside in the taste buds located in the papillae of the tongue. Taste buds relay information to the brain on the nutrient content of food and the presence of poisons. Recent advances in biochemical and physiological studies have enabled researchers to conclude that bitter taste transduction is mediated by so-called G-protein coupled receptors (GPCRs). GPCRs are 7 transmembrane domain cell surface proteins that amplify signals generated at a cell surface when the receptor interacts with a ligand (a tastant) whereupon they activate heterotrimeric G-proteins. The G-proteins are protein complexes that are composed of alpha and beta-gamma sub-units. They are usually referred to by their alpha subunits and classified generally into 4 groups: $G_{alpha\ s,\ i,\ q}$ and $_{12}$. The $G_{alpha\ q}$ type couple with GPCRs to activate phospholipase C which leads to an increase in cellular $Ca^{2+}$. There are many $G_q$-type G-proteins that are promiscuous and can couple to GPCRs, including taste receptors, and these so-called "promiscuous" G-proteins are well known in the art. These G-proteins dissociate into alpha and beta-gamma subunits upon activation, resulting in a complex cascade of cellular events that results in the cell producing second messengers, such as calcium ions, that enable the cells to send a signal to the brain indicating a bitter response.

There is also anatomical evidence that GPCRs mediate bitter taste transduction: clusters of these receptors are found in mammalian taste cells containing gustducin. Gustducin is a G-protein subunit that is implicated in the perception of bitter taste in mammals see, for example, Chandrashekar, J. et al. (2000) Cell 100: 703-711; Matsunami H. et al. (2000) Nature 404: 601-604; or Adler E. et al. (2000) Cell 100: 693-702. cDNAs encoding such GPCRs have been identified, isolated, and used as templates to compare with DNA libraries using in-silico data-mining techniques to identify other related receptors. In this manner it has been possible to identify a family of related receptors, the so-called T2R family of receptors, that have been putatively assigned as bitter receptors.

Humans are able to detect with a limited genetic repertoire of about 30 receptor genes thousands of different bitter compounds. Since their discovery in the year 2000 (Adler E. et al. (2000) supra; Chandrashekar J. et al. (2000) supra; Matsunami H. et al (2000) supra) only few mammalian TAS2Rs have been deorphanised, i.e. ligands, in particular agonists have been identified. The murine mTAS2R5 (Chandrashekar J. et al (2000) supra) and the rat rTAS2R9 (Bufe B. et al. (2002) Nature Genetics 32:397-401) respond to the toxic bitter substance cycloheximide, the mouse mTAS2R8 and the human hTAS2R4 respond to high doses of denatonium and, to a lesser extend, to 6-n-propyl-2-thiouracil (Chandrashekar J. et al. (2000) supra), the human hTAS2R10 and hTAS2R16 respond selectively to strychnine and bitter β-glucopyranosides, respectively (Bufe B. et al. (2002) supra). Although for some TAS2Rs a limited promiscuity (mTAS2R8, hTAS2R4) or specificity for a group of chemically related compounds (hTAS2R16) was reported, the relative selectivity of ligand recognition by the receptors published to date does, by far, not explain the enormous number of bitter tastants recognised by the mammalian gustatory system. There are several possible mechanisms conceivable to increase the number of tastants recognised by a limited number of taste receptor genes, the simplest way would be to have receptors which exhibit a broad tuning to a great number of structurally divergent ligands.

The present inventors now surprisingly show that the human bitter receptor hTAS2R14 responds to a variety of bitter compounds and, thus, appears to be a bitter taste receptor with such a broad tuning. This makes the identification of antagonists for this receptor particularly attractive, since it can be envisioned that by blocking the hTAS2R14 receptor the bitter perception elicited by a wide variety of different bitter tastants can be decreased or blocked.

DESCRIPTION OF THE INVENTION

Unless otherwise defined, all technical and scientific terms used herein have the same meaning as commonly understood by one of ordinary skill in the art to which this invention pertains. In case of conflict, the present document, including definitions, will control, Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The present inventors have identified agonists for the hTAS2R14 bitter taste receptor, and have found that it responds with specificity toward several classes of bitter compounds that are important in the food and pharmaceutical industries. The agonists provided by the present inventors enables the skilled person to design intelligent compound libraries to screen for antagonists to the bitter response of these receptors, which in turn enables the development of compounds and compositions to suppress or eliminate bitter tasting components of foods, in particular animal foods, nutrients and dietary supplements and pharmaceutical or homeopathic preparations containing such phyto-chemicals. Similarly, the invention also enables the skilled person to screen for additional bitter ligands, or even to screen for compounds that enhance a bitter response, such as might be useful in the food industry.

Therefore, in one aspect the present invention provides a process for isolating an agonist or antagonist of hTAS2R14 bitter taste receptor activity, wherein the hTAS2R14 bitter taste receptor is encoded by a polynucleotide selected from the group consisting of:
(a) a polynucleotide encoding at least the mature form of the polypeptide having the deduced amino acid sequence as shown in SEQ ID NO: 1;
(b) a polynucleotide having the coding sequence, as shown in SEQ ID NO: 2 encoding at least the mature form of the hTAS2R14 polypeptide;
(c) polynucleotides encoding a fragment or derivative of a polypeptide encoded by a polynucleotide of any one of (a) to (b), wherein in said derivative one or more amino acid residues are conservatively substituted compared to said polypeptide, and said fragment or derivative has hTAS2R14 bitter taste receptor activity;
(d) polynucleotides which are at least 50% identical to a polynucleotide as defined in any one of (a) to (c) and which code for a polypeptide having hTAS2R14 bitter taste receptor activity; and
(e) polynucleotides the complementary strand of which hybridizes, preferably under stringent conditions to a polynucleotide as defined in any one of (a) to (d) and which code for a polypeptide having hTAS2R14 bitter taste receptor activity,
comprising:
(1) contacting a polypeptide encoded by said polynucleotide, a host cell genetically engineered with said polynucleotide or with a vector containing said polynucleotide with a potential antagonist or potential agonist;
(2) determining whether the potential antagonists antagonizes or the potential agonist agonizes the bitter taste receptor activity of said polypeptide
wherein prior, concomitantly and/or after step (1) said polypeptide, said host cell or said vector is contacted with an agonist selected from the group consisting of 1,8-naphthaldehydic acid, 1-naphthoic acid, 1-nitronaphthalene, picrotin, picrotoxinin, piperonylic acid, sodium benzoate, (−)-α-thujone, parthenolide, herbolide A, herbolide D acetate, hydroxy-8α-parthenolide, pseudo-artabsine, and functional derivates thereof.

The polynucleotide employed in this process encodes a polypeptide that still exhibits essentially the same activity as the mature hTAS2R14 bitter taste receptor, i.e. has "bitter taste receptor activity". Preferably the polypeptide has at least 20% (e.g., at least: 20%; 30%; 40%; 50%; 60%; 70%; 80%; 90%; 95%; 98%; 99%; 99.5%; or 100% or even more) of the activity of the full-length hTAS2R14. One preferred way of measuring hTAS2R14 activity is the ability to release intracellular calcium in a heterologous cell expression system like, for example, (HEK293/15) that stably expresses the alpha-subunit of promiscuous G-proteins, e.g. the mouse $G_{15}$ subunit or chimeric versions thereof, in response to bitter tastants, which is dependent on the expression of polypeptides encoded by the polynucleotides of the present invention. The amount of intracellular calcium released can be monitored by, for example, the in vitro FLIPR assay described herein but also by the measurement of one of a variety of other parameters including, for example, $IP_3$ or cAMP. Additional ways of measuring G-protein coupled receptor activity are known in the art and comprise without limitation electrophysiological methods, transcription assays, which measure, e.g. activation or repression of reporter genes which are coupled to regulatory sequences regulated via the respective G-protein coupled signalling pathway, such reporter proteins comprise, e.g., CAT or LUC; assays measuring internalization of the receptor; or assays in frog melanophore systems, in which pigment movement in melanophores is used as a read out of the activity of adenylate cyclase or phospholipase C (PLC), which in turn are coupled via G-proteins to exogenously expressed receptors (see, for example, McClintock T. S. et al. (1993) Anal. Biochem. 209: 298-305; McClintock T. S. and Lerner M. R. (1997) Brain Res. Brain, Res. Protoc. 2: 59-68, Potenza M N (1992) Pigment Cell Res. 5: 372-328, and Potenza M. N. (1992) Anal. Biochem. 206: 315-322)

The term "potential antagonist", comprises any perceivable chemical substance or combination thereof in a non-purified, partially purified or purified state, however, an antagonist of hTAS2R14 bitter taste receptor activity is a substance which lowers the hTAS2R14 bitter taste receptor activity determined in the absence of the antagonist by at least 10% (e.g., at least: 1%, 15% 20%; 30%; 40%; 50%; 60%; 70%; 80%; 90%; 95%; 98%; 99%; 99.5%; or 100%) once contacted with the bitter taste receptor. Preferably the antagonist exerts this action when prior, concomitantly or after the contacting with the antagonist the hTAS2R14 polypeptide, the host cell expressing the hTAS2R14 polypeptide or the vector comprising the hTAS2R14 polypeptide is contacted with one of the identified hTAS2R14 agonists.

The term "potential agonist", comprises any perceivable chemical substance or combination thereof in a non-purified, partially purified or purified state and which elicits a bitter taste receptor activity, which is at least 10%, preferably 20%, 30%, 40%, 50%, 60%, 70%, 80%, 90%, 100%, 150%, 200% or more of the bitter taste receptor activity detected when identical molar concentration of 1,8-naphthaldehydic acid, 1-naphthoic acid, 1-nitronaphthalene, picrotin, picrotoxinin, piperonylic acid, sodium benzoate, (−)-α-thujone, parthenolide, herbolide A, herbolide D acetate, hydroxyl-8α-parthenolide or pseudoartabsine and functional derivatives thereof are contacted with the polypeptide, the host cell or vector. The activity of a potential agonist is preferably within the claimed ranges if compared to (−)-α-thujone, herbolide A or hydroxyl-8α-parthenolide.

The hTAS2R14 polynucleotide molecules usable in the method of the present invention can be DNA, cDNA, genomic DNA, synthetic DNA, or, RNA, and can be double-stranded or single-stranded, the sense and/or an antisense strand. Segments of these molecules are also considered within the scope of the invention, and can be produced by, for example, the polymerase chain reaction (PCR) or generated by treatment with one or more restriction endonucleases. A ribonucleic acid (RNA) molecule can be produced by in vitro transcription.

The polynucleotide molecules useable in the method of the present invention can contain naturally occurring sequences, or sequences that differ from those that occur naturally, but, due to the degeneracy of the genetic code, encode the same polypeptide (for example, the polypeptide with SEQ ID NO: 1). In addition, these nucleic acid molecules are not limited to coding sequences, e.g., they can include some or all of the non-coding sequences that lie upstream or downstream from a coding sequence.

The polynucleotide molecules of the invention can be synthesized in vitro (for example, by phosphoramidite-based synthesis) or obtained from a cell, such as the cell of a bacteria mammal. The nucleic acids can be those of a human but also derived from a non-human primate, mouse, rat, guinea pig, cow, sheep, horse, pig, rabbit, dog, or cat as long as they fulfill the criteria set out above. Combinations or modifications of the nucleotides within these types of nucleic acids are also encompassed.

In addition, the polynucleotides useable in the method of the present invention can encompass segments that are not found as such in the natural state. Thus, the invention encompasses recombinant nucleic acid molecules incorporated into a vector (for example, a plasmid or viral vector) or into the genome of a heterologous cell (or the genome of a homologous cell, at a position other than the natural chromosomal location). Recombinant nucleic acid molecules and uses therefore are discussed further below.

In certain preferred embodiments the method of the present invention uses isolated nucleic acid molecules which are at least 50% (or 55%, 65%, 75%, 85%, 95%, or 98%) identical to: (a) a nucleic acid molecule that encodes the polypeptide of SEQ ID NO: 2; (b) the nucleotide sequence of SEQ ID NO: 1; and (c) a nucleic acid molecule which includes a segment of at least 30 (e.g., at least 30, 40, 50, 60, 80, 100, 125, 150, 175, 200, 250, 300, 400, 500, 600, 700, 800, 850, 900, 951) nucleotides of SEQ ID NO: 1.

The determination of percent identity between two sequences is accomplished using the mathematical algorithm of Karlin and Altschul (1993) *Proc. Natl. Acad. Sci. USA* 90: 5873-5877. Such an algorithm is incorporated into the BLASTN and BLASTP programs of Altschul et al. (1990) J. Mol. Biol. 215: 403-410. BLAST nucleotide searches are performed with the BLASTN program, score=100, word length=12, to obtain nucleotide sequences homologous to HIN-1-encoding nucleic acids. BLAST protein searches are performed with the BLASTP program, score=50, wordlength=3, to obtain amino acid sequences homologous to the hTAS2R14 polypeptide. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used.

Hybridization can also be used as a measure of homology between two nucleic acid sequences. A nucleic acid sequence encoding hTAS2R14, or a portion thereof, can be used as a hybridization probe according to standard hybridization techniques. The hybridization of a hTAS2R14 probe to DNA or RNA from a test source (e.g., a mammalian cell) is an indication of the presence of the hTAS2R14 DNA or RNA in the test source. Hybridization conditions are known to those skilled in the art and can be found, for example, in Current Protocols in Molecular Biology, John Wiley & Sons, N.Y., 6.3.1-6.3.6, 1991. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are defined as equivalent to hybridization in 6× sodium chloride/sodium citrate (SSC) at 45° C., followed by a wash in 0.2×SSC, 0.1% SDS at 65° C.

The polynucleotides or proteins useable in the method of the present invention can be comprised in a vector containing the polynucleotide(s) or a protein encoded by above mentioned polynucleotide. The term "vector" refers to a protein or a polynucleotide or a mixture thereof which is capable of being introduced or of introducing the proteins and/or nucleic acid comprised therein into a cell. It is preferred that the proteins encoded by the introduced polynucleotide are expressed within the cell upon introduction of the vector.

In a preferred embodiment a vector useable in the method of the present invention comprises plasmids, phagemids, phages, cosmids, artificial mammalian chromosomes, knock-out or knock-in constructs, viruses, in particular adenoviruses, vaccinia viruses, attenuated vaccinia viruses, canary pox viruses, lentivirus (Chang, L. J. and Gay, E. E. (2001) Curr. Gene Therap. 1: 237-251), herpes viruses, in particular Herpes simplex virus (HSV-1, Carlezon, W. A. et al. (2000) Crit. Rev. Neurobiol. 14: 47-67), baculovirus, retrovirus, adeno-associated-virus (AAV, Carter, P. J. and Samulski, R. J. (2000) J. Mol. Med. 6:17-27), rhinovirus, human immune deficiency virus (HIV), filovirus and engineered versions thereof (see, for example, Cobinger G. P. et al. (2001) Nat. Biotechnol. 19:225-30), virosomes, "naked" DNA liposomes, and nucleic acid coated particles, in particular gold spheres. Particularly preferred are viral vectors like adenoviral vectors or retroviral vectors (Lindemann et al. (1997) Mol. Med. 3: 466-76 and Springer et al. (1998) Mol. Cell. 2: 549-58). Liposomes are usually small unilamellar or multilamellar vesicles made of cationic, neutral and/or anionic lipids, for example, by ultrasound treatment of liposomal suspensions. The DNA can, for example, be ionically bound to the surface of the liposomes or internally enclosed in the liposome. Suitable lipid mixtures are known in the art and comprise, for example, DOTMA (1,2-Dioleyloxypropyl-3-trimethylammoniumbromid) and DPOE (Dioleoyl-phosphatidyl-ethanolamin) which both have been used on a variety of cell lines.

Nucleic acid coated particles are another means for the introduction of nucleic acids into cells using so called "gene guns", which allow the mechanical introduction of particles into cells. Preferably the particles itself are inert, and therefore, are in a preferred embodiment made out of gold spheres.

In a further aspect polynucleotides useable in the method of the present invention are operatively linked to expression control sequences allowing expression in prokaryotic and/or eukaryotic host cells. The transcriptional/translational regulatory elements referred to above include but are not limited to inducible and non-inducible, constitutive, cell cycle regulated, metabolically regulated promoters, enhancers, operators, silencers, repressors and other elements that are known to those skilled in the art and that drive or otherwise regulate gene expression. Such regulatory elements include but are not limited to regulatory elements directing constitutive expression like, for example, promoters transcribed by RNA polymerase III like, e.g., promoters for the snRNA U6 or scRNA 7SK gene, the cytomegalovirus hCMV immediate early gene, the early or late promoters of SV40 adenovirus, viral promoter and activator sequences derived from, e.g., NBV, HCV, HSV, HPV, EBV, HTLV, MMTV or HIV; which allow inducible expression like, for example, CUP-1 promoter, the tet-repressor as employed, for example, in the tet-on or tet-off systems, the lac system, the trp system; regulatory elements directing tissue specific expression, preferably taste bud specific expression, e.g., PLCβ2 promoter or gustducin promoter, regulatory elements directing cell cycle specific expression like, for example, cdc2, cdc25C or cyclin A; or the TAC system, the TRC system, the major operator and promoter regions of phage A, the control regions of fd coat protein, the promoter for 3-phosphoglycerate kinase, the promoters of acid phosphatase, and the promoters of the yeast α- or a-mating factors.

As used herein, "operatively linked" means incorporated into a genetic construct so that expression control sequences effectively control expression of a coding sequence of interest.

Similarly, the polynucleotides useable in the method of the present invention can form part of a hybrid gene encoding additional polypeptide sequences, for example, a sequence that functions as a marker or reporter. Examples of marker and reporter genes include β-lactamase, chloram-phenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyl-transferase (XGPRT). As with many of the standard procedures associated with the practice of the method of the invention, skilled artisans will be aware of additional useful reagents, for example, additional sequences that can serve the function of a marker or reporter. Generally, the hybrid polypeptide will include a first portion and a second portion; the first portion being one or more hTAS2R14 polypeptide and the second portion being, for example, the reporter(s) described above or an Ig constant region or part of an Ig constant region, e.g., the CH2 and CH3 domains of IgG2a heavy chain. Other hybrids could include an antigenic tag or His tag to facilitate purification and/or detection. Recombinant nucleic acid molecules can also contain a polynucleotide sequence encoding the hTAS2R14 polypeptide operatively linked to a heterologous signal sequence. Such signal sequences can direct the protein to different compartments within the cell and are well known to someone of skill in the art. A preferred signal sequence is a sequence that facilitates secretion of the resulting protein.

Another aspect of the present invention is the use of a host cell genetically engineered with a polynucleotide or a vector as outlined above. The host cells that may be used in the method of the present invention include but are not limited to prokaryotic cells such as bacteria (for example, *E. coli* and *B. subtilis*), which can be transformed with, for example, recombinant bacteriophage DNA, plasmid DNA, or cosmid DNA expression vectors containing the polynucleotide molecules of the invention; simple eukaryotic cells like yeast (for example, *Saccharomyces* and *Pichia*), which can be transformed with, for example, recombinant yeast expression vectors containing the polynucleotide molecule of the invention; insect cell systems like, for example, Sf9 of Hi5 cells, which can be infected with, for example, recombinant virus expression vectors (for example, baculovirus) containing the polynucleotide molecules; Xenopus oocytes, which can be injected with, for example, plasmids; plant cell systems, which can be infected with, for example, recombinant virus expression vectors (for example, cauliflower mosaic virus (CaMV) or tobacco mosaic virus (TMV)) or transformed with recombinant plasmid expression vectors (for example, Ti plasmid) containing a hTAS2R14 nucleotide sequence; or mammalian cell systems (for example, COS, CHO, BHK, HEK293, VERO, HeLa, MDCK, Wi38, and NIH 3T3 cells), which can be transformed with recombinant expression constructs containing, for example, promoters derived, for example, from the genome of mammalian cells (for example, the metal-lothionein promoter) from mammalian viruses (for example, the adenovirus late promoter and the vaccinia virus 7.5 K promoter) or from bacterial cells (for example, the tet-repressor binding its employed in the tet-on and tet-off systems). Also useful as host cells are primary or secondary cells obtained directly from a mammal and transfected with a plasmid vector or infected with a viral vector. Depending on the host cell and the respective vector used to introduce the polynucleotide of the invention the polynucleotide can integrate, for example, into the chromosome or the mitochondrial DNA or can be maintained extrachromosomally like, for example, episomally or can be only transiently comprised in the cells.

In a preferred embodiment, the hTAS2R14 expressed by such cells are functional, i.e., upon binding to one or more bitter molecules they trigger an activation pathway in the cell. The cells are preferably mammalian (e.g., human, non-human primate, horse, bovine, sheep, pig, dog, cat, goat, rabbit, mouse, rat, guinea pig, hamster, or gerbil) cells, insect cells, bacterial cells, or fungal (including yeast) cells.

The polypeptides useable in the method of the invention include all those disclosed herein and functional fragments of these polypeptides. "Polypeptide" and "protein" are used interchangeably and mean any peptide-linked chain of amino acids, regardless of length or posttranslational modification. As used herein, a functional fragment of the hTAS2R14 is a fragment of the hTAS2R14 that is shorter than the full-length hTAS2R14 but that has at least 20% (e.g., at least: 20%; 30%; 40%; 50%; 60%; 70%; 80%; 90%; 95%; 98%; 99%; 99.5%; or 100% or even more) of the ability of the full-length hTAS2R14 to be stimulated by one of the bitter substances identified herein. Binding assays and bitter substances are described in more detail herein below. The polypeptides can also include fusion proteins that contain either a full-length hTAS2R14 polypeptide or a functional fragment of it fused to an unrelated amino acid sequence. The unrelated sequences can be additional functional domains or signal peptides. Signal peptides are described in greater detail and exemplified below.

The polypeptides can be any of those described above but with not more than 50 (e.g., not more than: 50, 45, 40, 35, 30, 25, 20, 15, 14, 13, 12, 11, 10, nine, eight, seven, six, five, four, three, two, or one) conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. All that is required of a polypeptide having one or more conservative substitutions is that it has at least 20% (e.g., at least: 20%; 30%; 40%; 50%; 60%; 70%; 80%; 90%; 95%; 98%; 99%; 99.5%; or 100% or even more) of the ability of the full-length hTAS2R14 to be stimulated by the respective bitter substance.

Polypeptides and fragments of the polypeptides useable in the method of the present invention can be modified, for example, for in vivo use by the addition of blocking agents, at the amino- and/or carboxyl-terminal ends, to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

The antagonists or agonists of the bitter taste receptors identified herein are of great importance for specific stimulation of a given bitter taste receptor and identification of substances that antagonize it, respectively.

The term "contacting" in the context of the present invention means any interaction between the antagonist and/or agonist with the polypeptide or the host cell, whereby any of the at least two components can be independently of each other in a liquid phase, for example in solution, or in suspension or can be bound to a solid phase, for example, in the form of an essentially planar surface or in the form of particles, pearls or the like. In a preferred embodiment a multitude of different compounds are immobilized on a solid surface like, for example, on a compound library chip and the protein of the present invention is subsequently contacted with such a chip. In another preferred embodiment the host cells genetically engineered with a polynucleotide encoding hTAS2R14 or with a vector containing such a polynucleotide express the hTAS2R14 bitter taste receptor at the cell surface and are contacted separatley in small containers, e. g., microtitre plates, with various compounds.

The term "functional derivatives thereof" refers to agonists, which are derived from the respectively indicated agonist, i.e. bitter substance by chemical modification and which elicit at least 20% (e.g., at least: 20%; 30%; 40%; 50%; 60%; 70%; 80%; 90%; 95%; 98%; 99%; 99.5%; or 100% or even more) of the bitter taste receptor activity, if compared to the respective unmodified bitter substance. Chemical modification includes without limitation the introduction of one or more, preferably two, three or four novel side chains or residues or the exchange of one or more functional groups like, for example, introduction or exchange of H; linear or branched alkyl, in particular lower alkyl ($C_1$, $C_2$, $C_3$, $C_4$, and $C_5$, e.g. methyl, ethyl, n-propyl, isopropyl, n-butyl, isobutyl, tert-butyl, n-pentyl or iso-pentyl); substituted linear or branched alkyl, in particular lower substituted alkyl; linear or branched alkenyl, in particular lower alkenyl ($C_2$, $C_3$, $C_4$ and $C_5$, e.g. ethenyl, 1-propenyl, 2-propenyl, iso-propenyl, 1-butenyl, 2-butenyl, 3-butenyl; substituted linear or branched alkenyl, in particular lower substituted alkenyl; linear or branched alkinyl, in particular lower alkinyl ($C_2$, $C_3$, $C_4$ and $C_5$); substituted linear or branched alkinyl, in particular lower substituted alkinyl; linear or branched alkanol, in particular lower alkanol ($C_1$, $C_2$, $C_3$, $C_4$, and $C_5$); linear or branched alkanal, in particular lower alkanal ($C_1$, $C_2$, $C_3$, $C_4$, and $C_5$, e.g. COH, $CH_2COH$, $CH_2CH_2COH$; aryl, in particular phenyl; substituted aryl, in particular substituted aryl; heteroaryl; substituted heteroaryl; alkylaryl, in particular benzyl; substituted alkylaryl; in particular substituted benzyl; alkylheteroaryl; substituted alkylheteroaryl; aminoalkyl, $C_1$, $C_2$, $C_3$, $C_4$ and $C_5$, e.g. $—NHCH_3$, $—NHCH_2CH3$, $—N(CH_3)_2$; substituted aminoalkyl; aminoketone, in particular $—NHCOCH_3$; substituted aminoketone; aminoaryl, in particular —NH-Ph; substituted aminoaryl, in particular substituted —NH-Ph; CN; $NH_2$; Halogen, in particular F, Cl, and Br; $NO_2$; OH; SH; NH; CN; or COOH group. If the residues mentioned above are substituted they are preferably mono, di, or tri substituted with a substituent selected from the group of halogen, in particular F, Cl, and Br, $NH_2$, $NO_2$, OH, SH, NH, CN, aryl, alkylaryl, heteroaryl, alkylheteroaryl, COH or COOH.

Preferred compounds that bind to the hTAS2R14 taste receptor are defined by the formula (I):

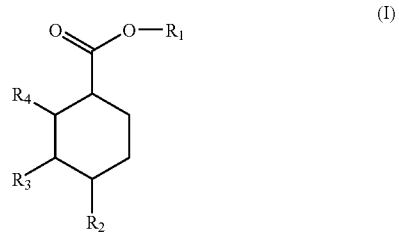

(I)

These compounds were studied in vitro (see Table I below) as is described in greater detail below. From these studies certain inferences can be drawn regarding the affinity of the compounds towards activation of the hTAS2R14 receptor. Whereas $R_1$ preferably means hydrogen, however, it is also possible that $R_1$ is not representing a substituent but is a free valence of a negatively charged "O" residue the change of which is satisfied by an alkali or earth alkali metal ion, preferably $Na^+$, $K^+$, $Li^+$, $Mg^{2+}$ or $Ca^{2+}$. Thus, in a preferred embodiment compounds according to formula (I) are used for agonizing or antagonizing hTAS2R14 function.

$R_2$, $R_3$ and $R_4$ in this formula can independently of each other mean hydrogen, $C_1$-$C_{10}$ alkyl, which may be branched, linear or cyclic as appropriate, particularly preferred alkyls are methyl, ethyl, n-propyl, isopropyl, n-butyl, isobutyl, tert-butyl, n-pentyl or iso-pentyl residues; lower alkenyl residues, preferably having two, three, four or five carbon atoms; lower alkynyl residues, preferably having two, three, four or five carbon atoms; lower alkoxy ($C_1$-$C_{10}$ alkoxy), particularly methoxy, ethoxy, propoxy or butoxy, which can in a preferred embodiment be further substituted with F, Cl, Br, $NH_2$, $NO_2$, OH, SH, NH, CN, aryl, heteroaryl, COH or COOH group; heteroaryl, e.g. benzofuran and cumarin; aryl, e.g. phenyl, naphtyl; F, Cl, Br, $NH_2$, $NO_2$, OH, SH, NH, CN, aryl, alkylaryl, heteroaryl, alkylheteroaryl, COH or COOH group. In a further embodiment the residues $R_2$ and $R_3$ or $R_3$ and $R_4$ can form together with additional C and/or heteroatoms, preferably N, S or O further ring structures leading to 3, 4, 5, 6, 7, 8, 9 or 10 membered ring structures, preferably aromatic or heteroaromatic rings, preferably with a 5 or 6 membered ring structure. The one or more rings connected via $R_2$ and $R_3$ or $R_3$ and $R_4$ can themselves be substituted as outlined above.

As a further step after measuring the antagonizing effect of a potential antagonist or agonist and after having measured the decrease or increase of bitter taste for at least two different potential antagonists or agonists at least one potential antagonist or agonist can be selected, for example, on grounds of the detected decrease of intracellular release of calcium, if compared to contacting with the known agonist alone.

The thus selected (potential) antagonist or agonist is than in a preferred embodiment modified in a further step. Modification can be effected by a variety of methods known in the art, which include without limitation the introduction of one or more, preferably two, three or four novel side chains or residues or the exchange of one or more functional groups like, for example, introduction or exchange of halogens, in particular F, Cl or Br; the introduction or exchange of lower alkyl residues, preferably having one to five carbon atoms like, for example, methyl, ethyl, n-propyl, isopropyl, n-butyl, isobutyl, tert-butyl, n-pentyl or iso-pentyl residues; lower alkenyl residues, preferably having two, three, four or five carbon atoms; lower alkinyl residues, preferably having two, three, four or five carbon atoms, which can in a preferred embodiment be further substituted with F, Cl, Br, $NH_2$, $NO_2$, OH, SH, NH, CN, aryl, heteroaryl, COH or COOH group; or the introduction of, for example, one or more residue(s) selected from the group consisting of $NH_2$, $NO_2$, OH, SH, NH, CN, aryl, alkylaryl, heteroaryl, alkylheteroaryl, COH or COOH group.

The thus modified (potential) antagonists or agonists are than individually tested with the method of the present invention, i.e. they are contacted with the polypeptide as such or with the polypeptide expressed in a host cell, which has been contacted prior, concomitantly or after step (1) with one of the identified agonists or derivatives thereof and subsequently activation of the bitter taste receptor activity by the modified agonists or antagonists is measured. This effect on the function of the hTAS2R14 protein can be measured, e.g. by the intracellular calcium release mediated. If needed the steps of selecting the antagonist or agonist, modifying the compound, contacting the antagonist or agonist with a polypeptide or a host cell and measuring of the activation of the bitter taste receptor activity can be repeated a third or any given number of times as required. The above described method is also termed "directed evolution" of an antagonist or agonist since it involves a multitude of steps including modification and selection, whereby antagonizing or agonizing compounds are selected in an "evolutionary" process optimizing their capabilities with respect to a particular property, e.g. their ability to inhibit, activate or modulate the activity of hTAS2R14, in particular inhibit or stimulate the intracellular release of calcium.

In order to express cDNAs encoding the receptors, one typically subclones receptor cDNA into an expression vector that contains a strong promoter to direct transcription, a transcription/translation terminator, and a ribosome-binding site for translational initiation. Suitable bacterial promoters are well known in the art, e.g., *E. coli, Bacillus* sp., and *Salmonella*, and kits for such expression systems are commercially available. Similarly eukaryotic expression systems for mammalian cells, yeast, and insect cells are well known in the art and are also commercially available. The eukaryotic expression vector may be, for example an adenoviral vector, an adeno-associated vector, or a retroviral vector.

In addition to the promoter, the expression vector typically contains a transcription unit or expression cassette that contains all the additional elements required for the expression of the receptor-encoding nucleic acid in host cells. A typical expression cassette thus contains a promoter operatively linked to the nucleic acid sequence encoding the receptor and signals required for efficient polyadenylation of the transcript, ribosome binding sites, and translation termination. The nucleic acid sequence encoding the receptor may typically be linked to a membrane-targeting signal such as the N-terminal 45 amino acids of the rat Somatostatin-3 receptor sequence to promote efficient cell-surface expression of the recombinant receptor. Additional elements of the cassette may include, for example enhancers.

An expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ, but there are many more known in the art to the skilled person that can be usefully employed.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A.sup.+, pMTO10/A.sup.+, pMAMneo-5, baculovirus pDSVE, pcDNA3.1, pIRES and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable.

The elements that are typically included in expression vectors also include a replicon that functions in *E. coli*, a gene encoding drug resistance to permit selection of bacteria that harbor recombinant plasmids, and unique restriction sites in nonessential regions of the plasmid to allow insertion of eukaryotic sequences. The particular drug resistance gene chosen is not critical, any of the many drug resistance genes known in the art are suitable. The prokaryotic sequences are optionally chosen such that they do not interfere with the replication of the DNA in eukaryotic cells, if necessary.

Standard transfection methods can be used to produce bacterial, mammalian, yeast or insect cell lines that express large quantities of the receptor, which are then purified using standard techniques.

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell. It is only necessary that the particular genetic engineering procedure used be capable of successfully introducing at least one gene into the host cell capable of expressing the receptor.

After the expression vector is introduced into the cells, the transfected cells may be cultured under conditions favoring expression of the receptor, which is recovered from the culture using standard techniques. For example the cells may be burst open either mechanically or by osmotic shock before being subject to precipitation and chromatography steps, the nature and sequence of which will depend on the particular recombinant material to be recovered. Alternatively, the recombinant protein may be recovered from the culture medium in which the recombinant cells had been cultured.

The activity of the receptor described herein can be assessed using a variety of in vitro and in vivo assays to determine functional, chemical, and physical effects, e.g., measuring ligand binding, secondary messengers (e.g., cAMP, cGMP, $IP_3$, DAG, or $Ca^{2+}$) ion flux, phosphorylation levels, transcription levels, neurotransmitter levels, and the like. Such assays are used in the method of the present invention to test for inhibitors of the receptors.

Samples or assays that are treated with a test compound may be compared to control samples without the test compound to examine the extent of modulation. Control samples either with or without known agonists or antagonists and untreated with test compound are assigned a relative receptor activity value of 100. Inhibition of receptor activity is achieved when the receptor activity value relative to the control is lower, and conversely receptor activity is enhanced when activity relative to the control is higher.

The effects of the test compounds upon the function of the receptors can be measured by examining any of the parameters described above. Any suitable physiological change that affects receptor activity can be used to assess the influence of a test compound on the receptors of this invention. When the functional consequences are determined using intact cells or animals, one can measure a variety of effects such as changes in intracellular secondary messengers such as $Ca^{2+}$, $IP_3$ or cAMP.

Preferred assays for G-protein coupled receptors include cells that are loaded with ion sensitive dyes to report receptor activity. In assays for identifying modulatory compounds, changes in the level of ions in the cytoplasm or membrane voltage will be monitored using an ion sensitive or membrane voltage fluorescent indicator, respectively. For G-protein coupled receptors, promiscuous G-proteins such as $G_\alpha 15$ and $G_\alpha 16$ and chimeric G-proteins can be used in the assay of choice (see, for example, Wilkie et al. (1991) Proc. Nat. Acad.

Sci. USA 88: 10049-10053). Such promiscuous G-proteins allow coupling of a wide range of receptors.

Receptor activation typically initiates subsequent intracellular events, e.g., increases in second messengers such as $IP_3$, which releases intracellular stores of calcium ions. Activation of some G-protein coupled receptors stimulates the formation of inositol triphosphate $IP_3$ through phospholipase C-mediated hydrolysis of phosphatidylinositol (Berridge & Irvine (1984) Nature 312: 315-21). $IP_3$ in turn stimulates the release of intracellular calcium ion stores. Thus, a change in cytoplasmic calcium ion levels, or a change in second messenger levels such as $IP_3$ can be used to assess G-protein coupled receptor function. Cells expressing such G-protein coupled receptors may exhibit increased cytoplasmic calcium levels as a result of contribution from both intracellular stores and via activation of ion channels, in which case it may be desirable, although not necessary, to conduct such assays in calcium-free buffer, optionally supplemented with a chelating agent such as EGTA, to distinguish fluorescence response resulting from calcium release from internal stores.

In a preferred embodiment, receptor activity is measured by expressing the hTAS2R14 receptor in a heterologous cell with a promiscuous G-protein, such as G.alpha.15, 16, or a chimeric G-protein that links the receptor to a phospholipase C signal transduction pathway. Optionally the cell line is HEK-293, although other mammalian cells are also preferred such as CHO and COS cells. Modulation of taste transduction is assayed by measuring changes in intracellular $Ca^{2+}$ levels, which change in response to modulation of the receptor signal transduction pathway via administration of a molecule that associates with the receptor. Changes in $Ca^{2+}$ levels are optionally measured using fluorescent $Ca^{2+}$ indicator dyes and fluorometric imaging.

The activity of the signalling molecule and the increase or decrease of that activity in response to the potential agonist or antagonist can be determined as outlined above with respect to the identification of bitter receptor taste activity. The respectively indicated percent increases or decreases of the activity, which are required to qualify as antagonist or agonist; do apply mutatis mutandis. Additionally the term "contacting" has the meaning as outlined above. Preferably the signalling molecule and/or the promiscuous G-protein has been introduced into the cell. The types of cell, which are preferred are those indicated above.

In yet another embodiment, the ligand-binding domains of the receptors can be employed in vitro in soluble or solid-state reactions to assay for ligand binding. Ligand binding in a receptor, or a domain of a receptor, can be tested in solution, in a bilayer membrane attached to a solid phase in a lipid monolayer or vesicles. Thereby, the binding of a modulator to the receptor, or domain, can be observed using changes in spectroscopic characteristics, e.g. fluorescence, absorbance or refractive index; or hydrodynamic (e.g. shape), chromatographic, or solubility properties, as is generally known in the art.

The compounds tested as modulators of the receptors can be any small chemical compound, or a biological entity, such as a protein, sugar, nucleic acid or lipid. Typically, test compounds will be small chemical molecules. Essentially any chemical compound can be used as a potential modulator or ligand in the assays of the invention, although knowledge of the ligand specificity of an individual receptor would enable the skilled person to make an intelligent selection of interesting compounds. The assays may be designed to screen large chemical libraries by automating the assay steps and providing compounds from any convenient source to assays, which are typically run in parallel (e.g., in microtiter formats on microtiter plates in robotic assays). The skilled person will understand that there are many suppliers of libraries of chemical compounds.

Assays may be run in high throughput screening methods that involve providing a combinatorial chemical or peptide library containing a large number of potential therapeutic or tastant compounds (that are potential ligand compounds). Such libraries are then screened in one or more assays, as described herein, to identify those library members (particular chemical species or subclasses) that display a desired characteristic activity. The compounds thus identified can serve as lead compounds to further develop modulators for final products, or can themselves be used as actual modulators.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art and no more needs to be stated here.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 different compounds is possible using the integrated systems of the invention.

Lead compounds found by assay technology herein above described, or development compounds formed from such leads can be administered directly to a human subject to modulate bitter taste. Alternatively, such compounds can be formulated with other ingredients of preparations to be taken orally, for example, foods, including animal food, and beverages, pharmaceutical or nutraceutical or homeopathic preparations.

Therefore, another aspect of the invention is a process for the production of foodstuffs or any precursor material or additive employed in the production of foodstuffs comprising the steps of the above described processes for the identification of an antagonist or agonist of hTAS2R14 and the subsequent step of admixing the identified compound or antagonist with foodstuffs or any precursor material or additive employed in the production of foodstuffs.

Bitter taste is a particular problem when orally administering pharmaceuticals, which often have an unpleasant bitter taste. In particular in elderly persons, children and chronically ill patients this taste can lead to a lack of compliance with a treatment regimen. In addition in veterinary applications the oral administration of bitter tasting pharmaceuticals can be problematic. Therefore, a further aspect of the invention is a process for the production of a nutraceutical or pharmaceutical composition comprising the step of the process to identify an antagonist or an agonist of hTAS2R14 and the subsequent step of formulating the compound or antagonist with an active agent in a pharmaceutically acceptable form.

Consequently, a further aspect of the invention is a foodstuff, in particular animal food, or any precursor material or additive employed in the production of foodstuffs produced according to the method of the invention.

Also comprised is a nutraceutical or pharmaceutical composition produced according to the method of the invention and at least one achieve agent and optinally pharmaceutically acceptable carrier and/or adjuvants.

The amount of compound to be taken orally must be sufficient to affect a beneficial response in the human subject, and will be determined by the efficacy of the particular taste modulators and the existence, nature, and extent of any adverse side-effects that accompany the administration of a particular compound.

A further aspect of the present invention is the use of an agonist of hTAS2R14 activity selected from the group consisting of 1,8-naphthaldehydic acid, 1-naphthoic acid, 1-nitronaphthalene, picrotin, picrotoxinin, piperonylic acid, sodium benzoate, (−)-α-thujone, parthenolide, herbolide A, herbolide D acetate, hydroxy-8α-parthenolide, pseudo-artabsine, and functional derivates thereof to enhance bitter taste.

A further aspect of the present invention is the use of an antagonist of hTAS2R14 identified with the method of the present invention for the reduction of bitter taste inducible by 1,8-naphthaldehydic acid, 1-naphthoic acid, 1-nitronaphthalene, picrotin, picrotoxinin, piperonylic acid, sodium benzoate, (−)-α-thujone, parthenolide, herbolide A, herbolide D acetate, hydroxy-8α-parthenolide, pseudo-artabsine, and functional derivates thereof.

The following figures and examples are merely illustrative of the present invention and should not be construed to limit the scope of the invention as indicated by the appended claims in any way.

EXAMPLES

Conditional Expression of hTAS2R14

Figure 1:
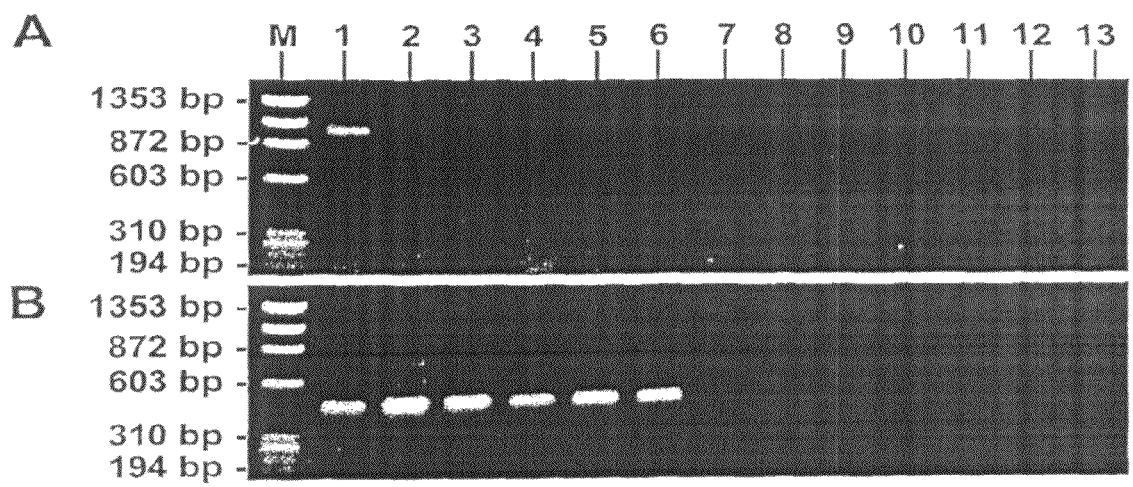
FIG. 1 RT-PCR analysis of hTAS2R14 gene expression in different human tissues. A) PCR-products specific for hTAS2R14, B) presence of cDNA as detected by GAPDH-specific oligonucleotides used as positive controls. M; molecular weight standard, 1; circumvallate papilla, 2; lingual epithelium containing no taste papillae, 3; salivary gland, 4; cerebellum, 5; kidney, 6; testis, 7; circumvallate papillae-RT (reverse transcriptase omitted to assess contaminating genomic DNA), 8; lingual epithelium-RT, 9; salivary gland-RT, 10; cerebellum-RT, 11; kidney-RT, 12; testis-RT 13; $H_2O$ control.
Figure 2:
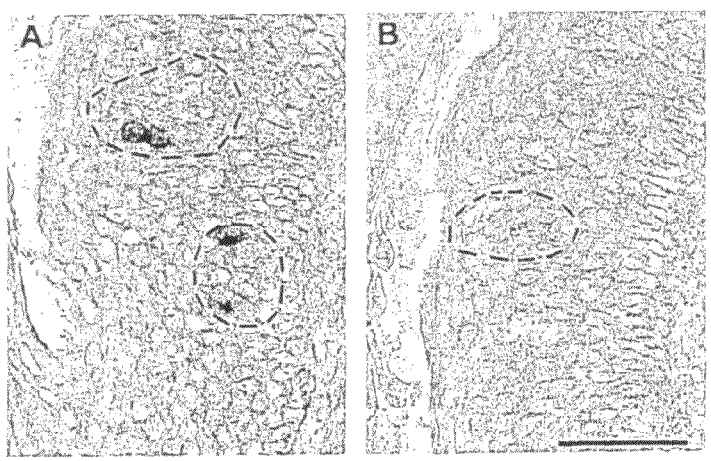
FIG. 2 In situ hybridisation of hTAS2R14 mRNA in human circumvallate papillae. 20 μm cryostat cross sections of human circumvallate papillae were hybridised with digoxigenin-labeled antisense (A) or sense (B) riboprobes. Taste buds are circled, Scale bar=50 μm.
Figure 3:
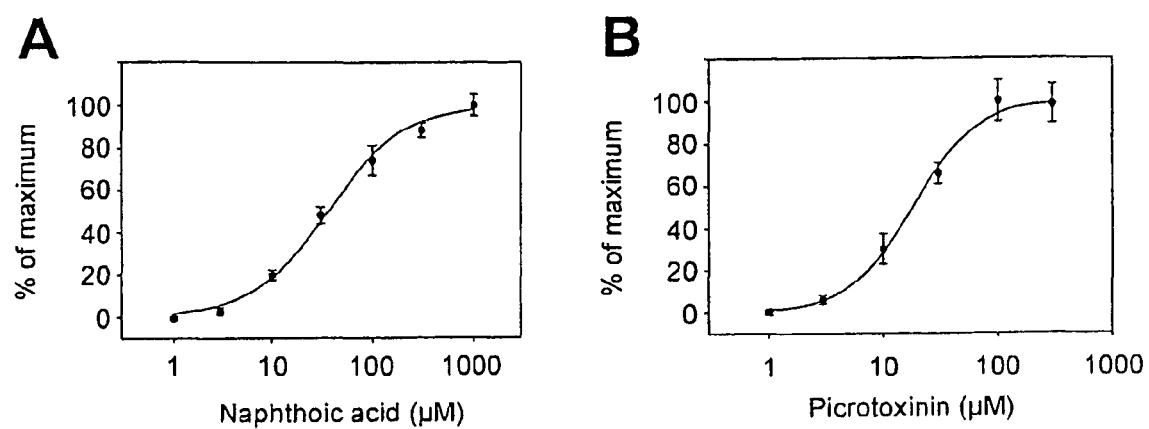
FIG. 3 Dose-response curves of picrotoxinin and 1-naphthoic acid. Different concentrations of 1-naphthoic acid (A) and picrotoxinin (B) were applied onto hTAS2R14 transfected cells. Dose-response curves and the corresponding $EC_{50}$ values of the effects of picrotoxinin and 1-naphthoic acid were calculated using sigma plot.

The cDNA of hTAS2R14 supplemented with an amino terminal export tag corresponding to amino acids 1-45 of rat somatostatin receptor 3 and a carboxy terminal HSV-tag was transiently transfected into HEK-293T cells stably expressing the chimeric G-protein subunit Gα16gust44 (Ueda T. et al. (2003) J. Neurosci. 23: 7376-7380) using Lipofectamine2000 (Invitrogen). Ligand screening using an automated fluorometric imaging plate reader (Molecular Devices) was done 24-32 hrs after transfection as described (Bufe B. et al. (2002) Nature Genetics 32: 397-401). Briefly: The cells were loaded with 4 μM FLUO-4/AM (Molecular Probes) and 0.04% Pluronic F-127 (Molecular Probes) in Hepes-buffered saline (HBS), 140 mM NaCl, 5 mM KCl, 2.5 mM CaCl2, 10 mM Hepes, 10 mM glucose and 2.5 mM probenicide, pH 7.4, for 1 hour at 37° C. Thereafter, cells were gently washed in HBS by an automated plate washer (Denley Cellwash, Labsystems) and transferred to the FLIPR (Molecular Devices). The FLIPR integrates an argon laser excitation source, a 96-well pipettor, and a detection system utilizing a Charged Coupled Device imaging camera. Fluorescence emissions from the 96 wells were monitored at an emission wavelength of 510 nm, after excitation with 488 nm (F488). Fluorescence data were collected 1 min before and 10 min after stimulation. Data were collected every 6 s before and every 1 s after agonist stimulation. 50 μl of 3× concentrated agonists (Sigma) dissolved in a suitable mixture of solution C1 (130 mM NaCl, 5 mM KCl, 10 mM Hepes, 2 mM $CaCl_2$, 10 mM glucose (pH 7.4) and DMSO not exceeding a final DMSO concentration of 1% (v/v)) were delivered within 2 s by the integrated 96-well pipettor to the wells containing 100 μl HBS. Agonist responses were quantified using the amplitudes of the fluorescence peaks. The responses of five wells containing cells expressing the same receptor and that received the same stimulus were averaged. Data were collected from two independent experiments carried out in triplicates. The dose-response curves were normalized to the maximal response observed. Results are shown in Table 1 below.

TABLE 1

A

| test substance | | conc (μM) | response | control |
|---|---|---|---|---|
| 1,8-naphthalde-hydic acid | 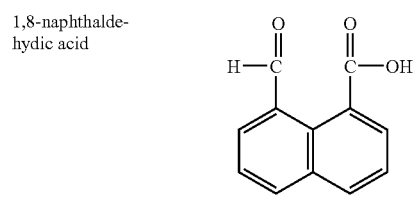 | 300 30 | | |

TABLE 1-continued
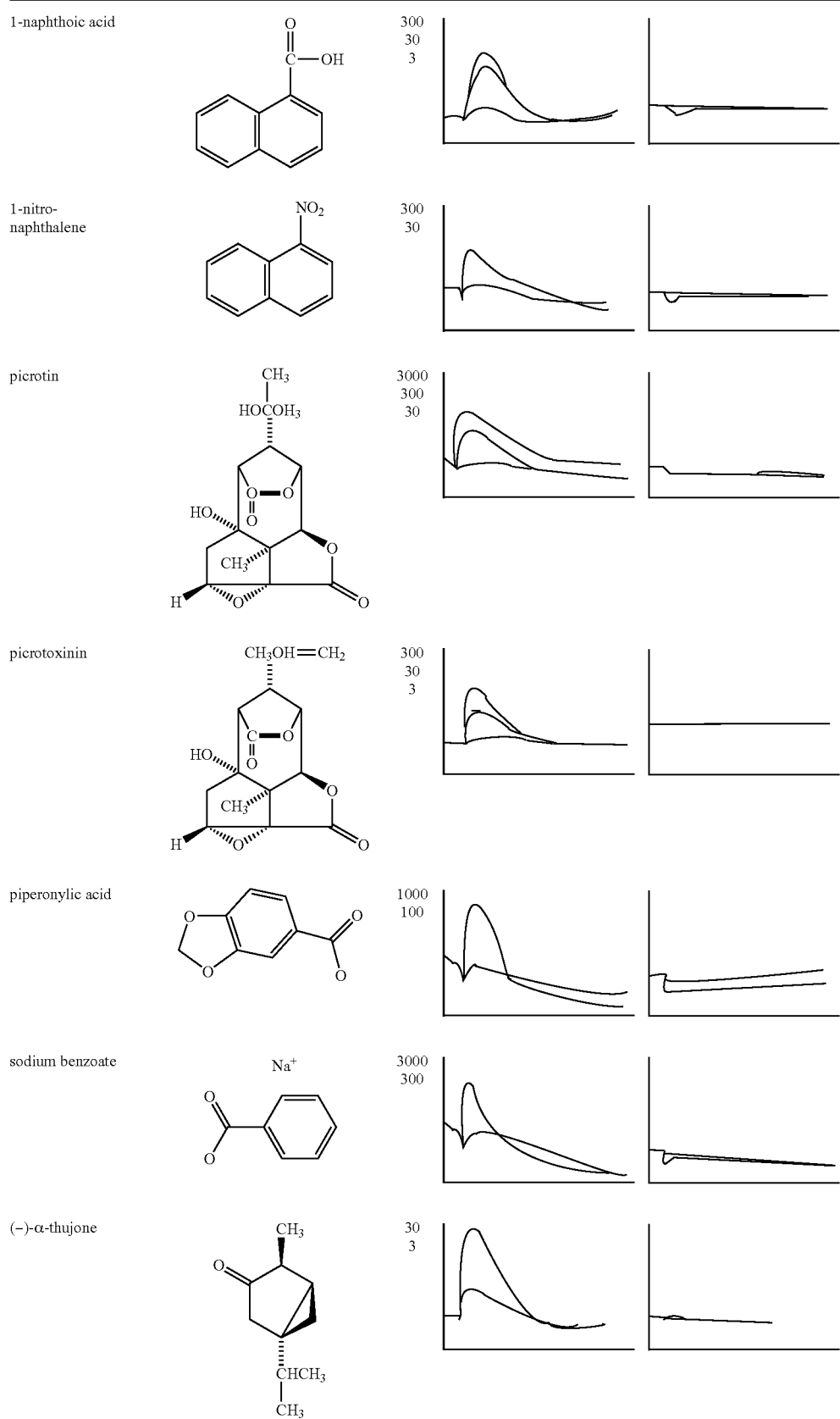

TABLE 1-continued
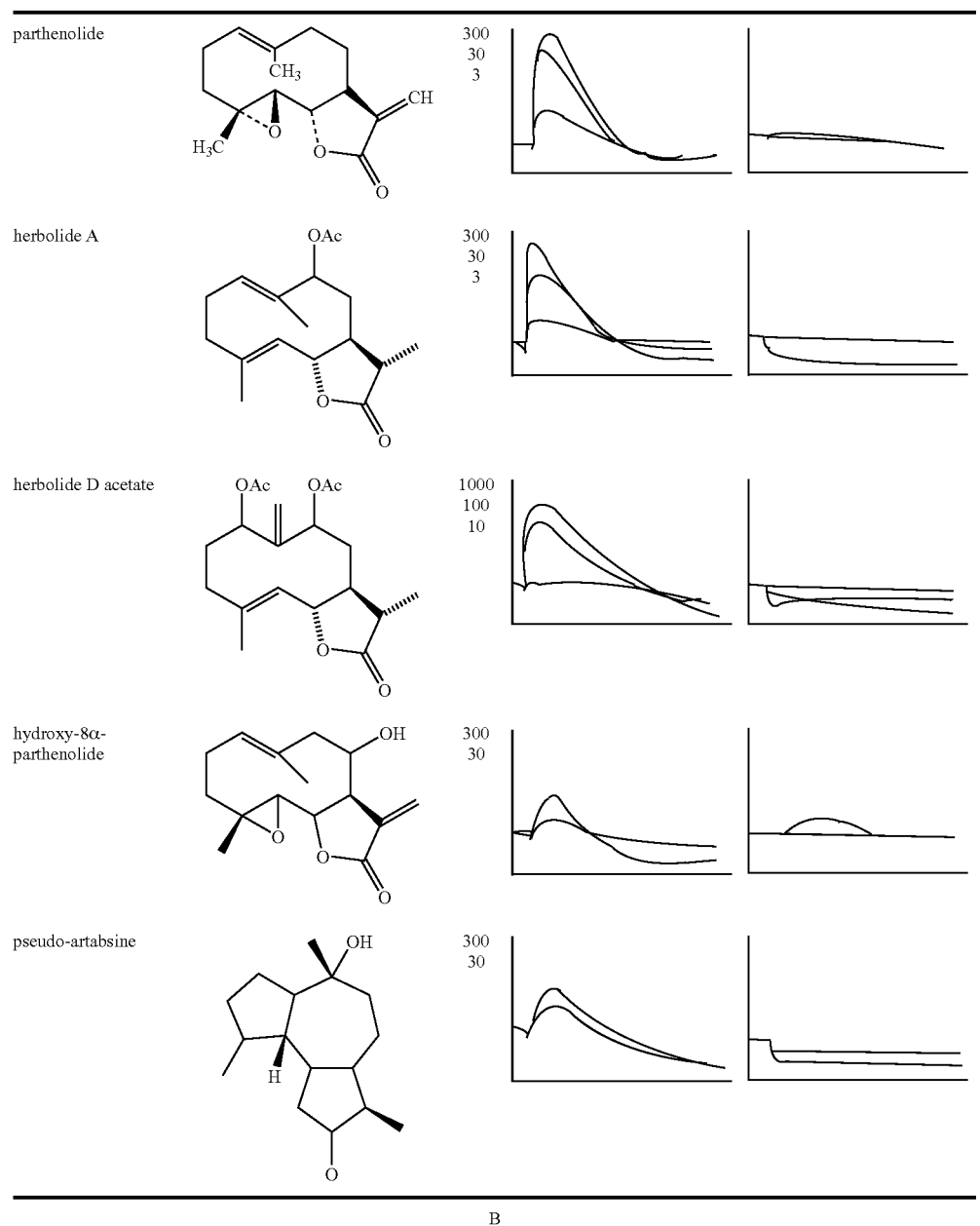

TABLE 1-continued

| | | | |
|---|---|---|---|
| antipyrine | *(structure)* | 500 | n.r. |
| atropine | *(structure)* | 300 | n.r. |
| benzoin | *(structure)* | 10 | n.r. |
| caffeic acid | *(structure)* | 30 | n.r. |
| caffeine | *(structure)* | 3000 | n.r. |
| carisoprodol | *(structure)* | 10 | n.r. |
| chloramphenicol | *(structure)* | 30 | n.r. |
| colchicine | *(structure)* | 3000 | n.r. |

TABLE 1-continued
| | | | |
|---|---|---|---|
| cromolyn sodium salt | 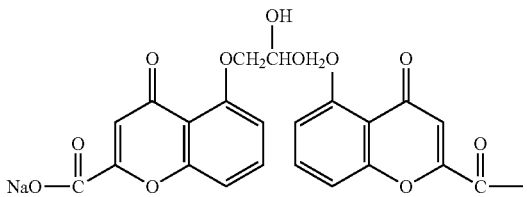 | 5000 | n.r. |
| cycloheximide | 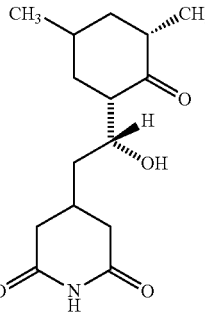 | 1000 | n.r. |
| dicyclomine hydrochloride | 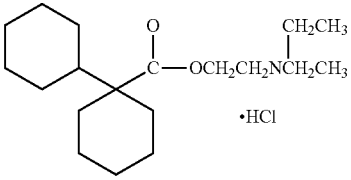 | 1 | n.r. |
| 9,10-dihydro-phenanthrene | 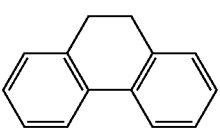 | 5 | n.r. |
| (−)-nicotine | 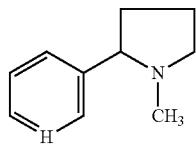 | 10 | n.r. |
| ouabain | 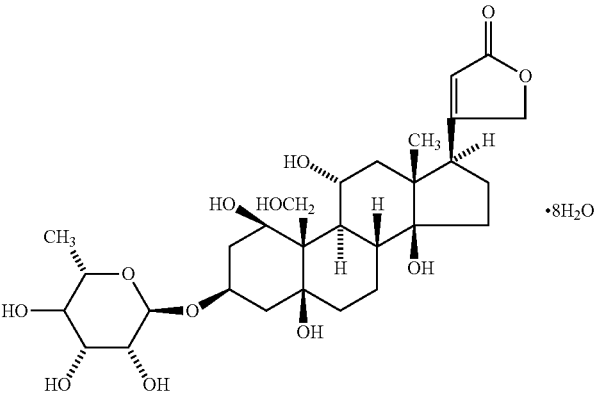 | 3000 | n.r. |
| D-phenylalanine | 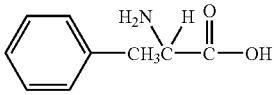 | 10000 | n.r. |
| L-phenylalanine | 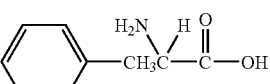 | 10000 | n.r. |

TABLE 1-continued

| | | | |
|---|---|---|---|
| phenyl-thiocarbamide (PTC) | (structure) | 1000 | n.r. |
| picric acid | (structure) | 524 | n.r. |
| 6-propyl-2-thiouracil (PROP) | (structure) | 100 | n.r. |
| quinine sulfate dihydrate | (structure) · $H_2CO_4$ · $H_2O$ | 50 | n.r. |
| D-(−)-salicin | (structure) | 10000 | n.r. |
| (−)-sparteine | (structure) · $H_2SO_4$ · $5H_2O$ | 500 | n.r. |
| strychnine nitrate | (structure) | 50 | n.r. |

TABLE 1-continued

| | | 500 | n.r. |
|---|---|---|---|
| D-(+)-sucrose octaacetate (SOA) | [chemical structure: sucrose octaacetate with R = —C(=O)—CN₃] | 500 | n.r. |

The substances used for the ligand screening are identified by their names (row 1) and their chemical structure (row 2). The concentrations tested for hTAS2R14 activation are listed in row 3. The fluorescence monitored as a result of an increase of the intracellular calcium concentration after stimulation with the different concentrations of compounds is shown in row 4. When applicable row 5 depicts responses of mock-transfected cells to the corresponding concentrations of compounds are depicted as negative controls. Vertical scale is 8000 counts, horizontal scale is 10 min. n.r.=no response. A) Compounds activating hTAS2R14, B) Compounds tested negative.

RT-PCR Analysis of Human Tissues

Specimens of human vallate papillae and papillae-free lingual epithelium were obtained with the written consent of volunteers and approved by the local ethical committee. Total RNA was extracted using TRIzol reagent (Invitrogen). Total RNAs from human cerebellum, salivary glands, kidney, and testis were purchased from BD Biosciences Clontech. RNAs were subjected to digestion with RNAse-free DNAse I (Invitrogen) and cDNA synthesis using the Smart cDNA synthesis kit (Clontech). For amplification of hTAS2R14 cDNA oligonucleotides R14_for 5'-GGCCAATTGGAAT-TCATGGGTGGTGTCATAAAGAGCATATTTACA-3' (SEQ ID NO. 3), and R14_rev 5'-TCCTCAATTGTCAT-CAGCGGCCGCCAGATGATTCTCTAAAT-TCTTTGTGACCTGAG-3' (SEQ ID NO. 4) were used. For controls the cDNA GAPDH was amplified with oligonucleotides GAPDH_for 5'-ACCACAGTCCATGCCATCAC-3' (SEQ ID NO. 5), and GAPDH_rev 5'-TCCCACCACCCT-GTTGCTGTA-3' (SEQ ID NO. 6). For negative controls reverse transcriptase was omitted during the cDNA synthesis. The PCR conditions for hTAS2R14 were: 5 min 94° C. pre-denaturation, 1 min 64° C., 1.5 min. 72° C., 0.5 min 94° C. for 3 cycles, followed by 35 cycles of 2.5 min 72° C., 0.5 min 94° C., and 15 min 72° C. for polishing of PCR products. For GAPDH amplification the following protocol was used: 5 min 94° C., 28 cycles; 45 s 58° C., 45 s 72° C., 30 s 94° C., and 5 min 58° C., 10 min 72° C.

In Situ Hybridization of Human Vallate Papilla

In situ hybridization was mainly done as before (Behrens et al. (2000) Europ. J. Neurosci. 12: 1372-1384). Briefly: 20 μm cross-sections of circumvallate papillae of human tongues were processed and thaw-mounted onto positively charged glass slides. Prior to hybridisation the sections were postfix-ated, permeabilised, and acetylated. Prehybridisation was done at 50° C. for 5 h, followed by hybridisation over night at 50° C. After hybridisation the slides were washed several times at low stringency, followed by RNAse. A treatment and high stringency washes using 0.4×SSC buffer at 50° C. Hybridised riboprobes were detected using an anti-Digoxi-genin antibody and colourimetry. Photomicrographs were taken with a CCD camera (RT slider, Diagnostic Instruments Inc.) mounted to a Zeiss Axioplan microscope.

The invention claimed is:

1. A process for identifying an agonist or antagonist of the ability of a receptor to release intracellular calcium in a heterologous cell expression system in response to an agonist selected from the group consisting of 1,8-naphthaldehydic acid, 1-naphthoic acid, 1-nitronaphthalene, picrotin, picrotoxinin, piperonylic acid, sodium benzoate, (−)-α-thujone, parthenolide, herbolide A, herbolide D acetate, hydroxy-8α-parthenolide, pseudo-artabsine, and functional derivatives thereof,
  wherein said receptor comprises a polypeptide is selected from the group consisting of:
    (a) a polypeptide comprising the amino acid sequence as shown in SEQ ID NO: 1; and
    (b) a polypeptide comprising an amino acid sequence having one to fifteen amino acids modified compared to SEQ ID NO: 1;
  comprising:
    (1) contacting said polypeptide or a host cell expressing said polypeptide with a potential antagonist or potential agonist; and
    (2) determining whether the potential antagonist antagonizes or the potential agonist agonizes said ability;
  wherein prior to, concomitant with, and/or after step (1), said polypeptide or said host cell is contacted with an agonist selected from the group consisting of 1,8-naphthaldehydic acid, 1-naphthoic acid, 1-nitronaphthalene, picrotin, picrotoxinin, piperonylic acid, sodium benzoate, (−)-α-thujone, parthenolide, herbolide A, herbolide D acetate, hydroxy-8α-parthenolide, pseudo-artabsine, and functional derivatives thereof,
  wherein said receptor has at least 20% of said ability of the full length receptor of SEQ ID NO: 1
  wherein the functional derivatives thereof refers to agonists with a chemical modification and the chemically-modified agonists elicit at least 20% of said ability if compared to the respective unmodified agonists,
  wherein chemical modification is the introduction of one or more side chains or residues or the exchange of one or more functional groups,
  wherein the side chains, residues, and functional groups are selected from H, linear or branched alkyl, lower alkyl, methyl, ethyl, n-propyl, isopropyl, n-butyl, isobutyl, tert-butyl, n-pentyl, iso-pentyl, substituted linear or branched alkyl, lower substituted alkyl, linear or branched alkenyl, lower alkenyl, ethenyl, 1-propenyl, 2-propenyl, iso-propenyl, 1-butenyl, 2-butenyl, 3-butenyl, substituted linear or branched alkenyl, lower substituted alkenyl, linear or branched alkinyl, substituted linear or branched alkinyl, lower substituted alkinyl, linear or branched alkanol, lower alkanol, linear or branched alkanal, lower alkanal, COH, CH$_2$COH, $CH_2CH_2COH$, aryl, phenyl, substituted aryl, heteroaryl, substituted heteroaryl, alkylaryl, benzyl, substituted alkylaryl, substituted benzyl, alkylheteroaryl, substituted alkylheteroaryl, aminoalkyl, —$NHCH_3$, —$NHCH_2CH3$, —$N(CH_3)_2$, substituted aminoalkyl, aminoketone, —$NHCOCH_3$, substituted aminoketone, aminoaryl, NH-Ph, substituted aminoaryl, substituted —NH-Ph, CN, $NH_2$, halogen, F, Cl, Br, $NO_2$, OH, SH, NH, CN, and COOH.

2. A process for the production of food, a precursor material or additive employed in the production of foodstuffs comprising the steps of the process of claim 1 and the subsequent step of admixing the identified antagonist or agonist with foodstuffs or precursor material or additive employed in the production of foodstuffs.

3. A process for the production of a nutraceutical or pharmaceutical composition comprising the steps of the process of claim 1 and the subsequent step of formulating the antagonist or agonist with an active agent in a pharmaceutically acceptable form.

* * * * *

UNITED STATES PATENT AND TRADEMARK OFFICE
CERTIFICATE OF CORRECTION

PATENT NO. : 8,158,372 B2
APPLICATION NO. : 11/578013
DATED : April 17, 2012
INVENTOR(S) : Maik Behrens et al.

It is certified that error appears in the above-identified patent and that said Letters Patent is hereby corrected as shown below:

Column 17,
Structure corresponding to picrotin,

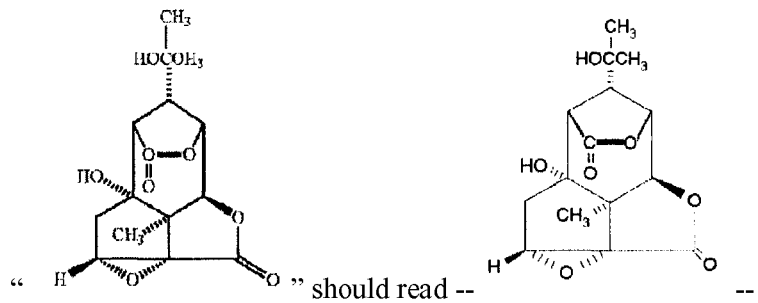

should read --

Structure corresponding to picrotoxinin,

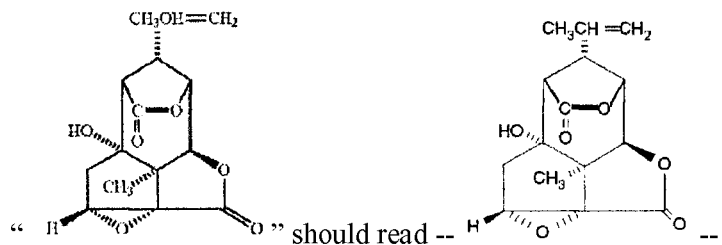

should read --

Column 19,
Structure corresponding to herbolide D acetate,

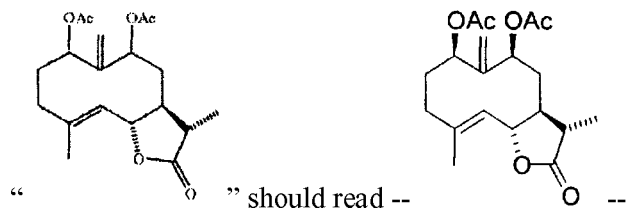

should read --

Signed and Sealed this
Thirty-first Day of July, 2012

David J. Kappos
*Director of the United States Patent and Trademark Office*

CERTIFICATE OF CORRECTION (continued)
U.S. Pat. No. 8,158,372 B2

Column 19,
Structure corresponding to hydroxy-8α-parthenolide,

" 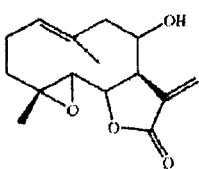 " should read -- 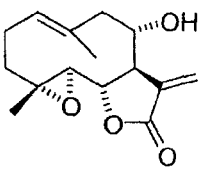 --

Structure corresponding to pseudo-artabsine,

" 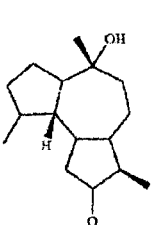 " should read -- 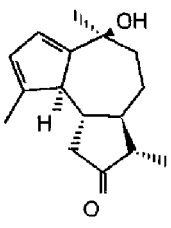 --

Column 21,
Structure corresponding to chloramphenicol,

" 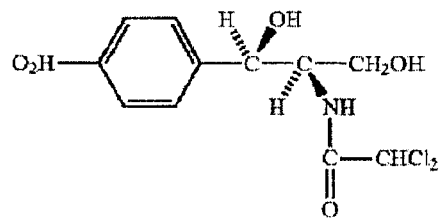 " should read -- 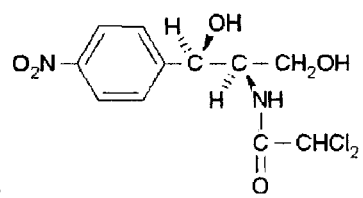 --

Column 23,
Structure corresponding to cromolyn sodium salt,

" 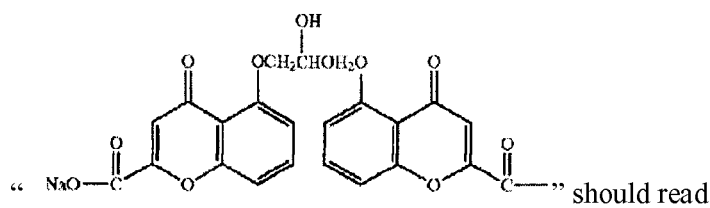 " should read

-- 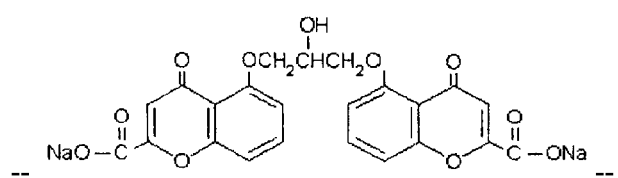 --

Structure corresponding to dicyclomine hydrochloride,

" 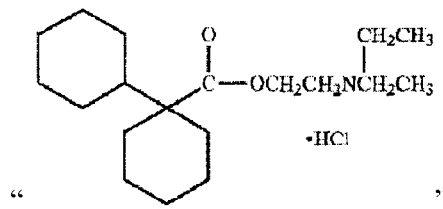 " should read -- 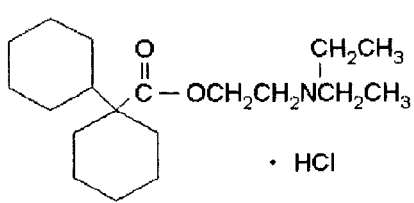 --

Column 23,
Structure corresponding to (-)-nicotine,
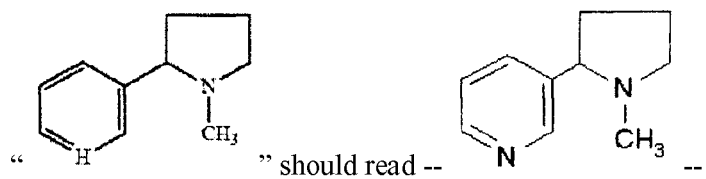 should read -- -- 
Structure corresponding to D-phenylalanine,
 should read -- --
Structure corresponding to L-phenylalanine,
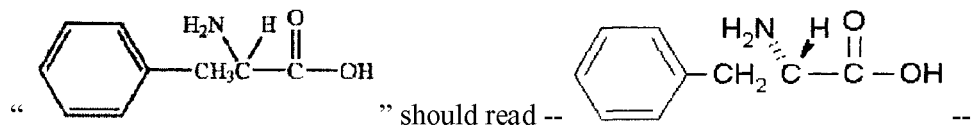 should read -- --
Column 25,
Structure corresponding to quinine sulfate dehydrate,
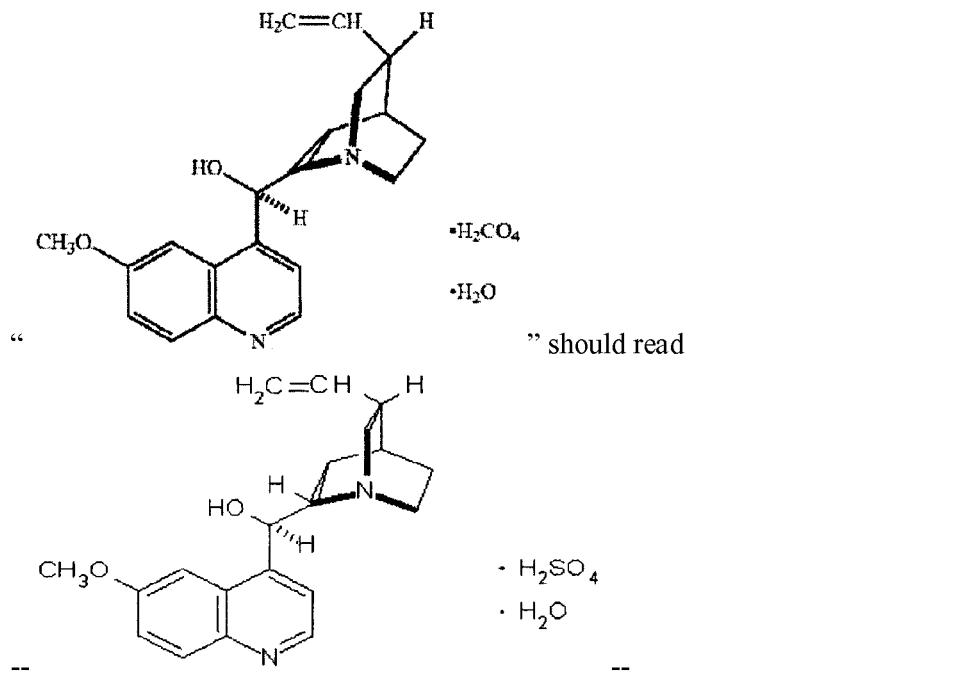
-- --

CERTIFICATE OF CORRECTION (continued)
U.S. Pat. No. 8,158,372 B2

Column 25,
Structure corresponding to (-)-sparteine,

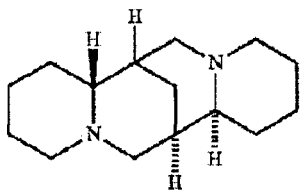 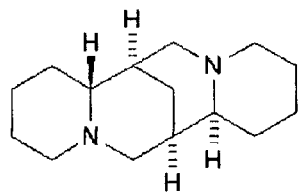

"   ·H₂SO₄    ·5H₂O   " should read --   · H$_2$SO$_4$   · 5H$_2$O   --

Structure corresponding with strychnine nitrate,

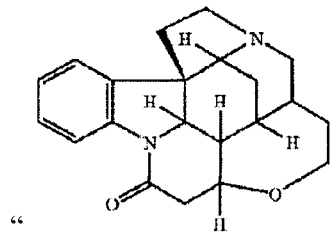 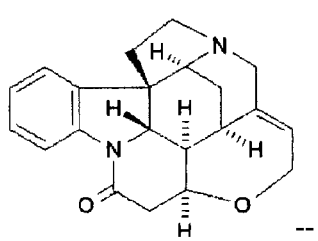

"                                    " should read --                          --